US006598457B2

(12) United States Patent
Sullivan et al.

(10) Patent No.: US 6,598,457 B2
(45) Date of Patent: Jul. 29, 2003

(54) METHOD AND APPARATUS FOR MEASURING THE AMOUNT OF ENTRAINED GASES IN A LIQUID SAMPLE

(75) Inventors: Raymond D. Sullivan, Collierville, TN (US); Billy R. Landreth, Memphis, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 0 days.

(21) Appl. No.: 09/826,555

(22) Filed: Apr. 5, 2001

(65) Prior Publication Data

US 2002/0144536 A1 Oct. 10, 2002

(51) Int. Cl.$^7$ .......................... G01N 33/497; G01N 7/00
(52) U.S. Cl. .................... 73/19.01; 73/19.03; 73/19.05; 73/19.1; 73/63; 73/53.03; 162/263; 162/198; 210/634; 210/637; 210/103; 210/746
(58) Field of Search ................................. 162/263, 198; 73/19.01, 19.03, 19.05, 19.06, 19.1, 61 R, 63, 32 R, 99.05, 53.03; 210/634, 637, 511, 76, 103, 746

(56) References Cited

U.S. PATENT DOCUMENTS

| | | | | |
|---|---|---|---|---|
| 4,746,930 A | * | 5/1988 | Szimazaki et al. | 346/76 |
| 5,394,339 A | * | 2/1995 | Jones | 364/510 |
| 5,470,484 A | | 11/1995 | McNeel | 210/746 |

OTHER PUBLICATIONS

Matula, Jouni P., "Presence of Entrained Air and Dissolved Gases in Paper Making Stock", Technical Article presented at TAPPSA '96, the 8$^{th}$ Southern African Pulp and Paper Conference in Durban.

Dougherty, Steve J., "Online Entrained–Air Measurement for Brownstock–Washer Defoamer Control", Tappi Journal, Jan. 1989, pp. 50–54.

Kortelainen, Helena, "Tools for Successful Wet–End Chemistry Control", Tappi Journal, Dec. 1992, pp. 112–117.

Matula, Jouni P., "Presence of Entrained Air and Dissolved Gases in Paper Making Stock", Technical Article.

Matula, et al., "How to Deal With Difficult Passengers", Wet End, presented at the 1996 PTS Symposium, Munich.

Lorenčak, et al., "Deaeration in High Temperature Systems", Paper Technology, Nov. 1997, pp. 25–28.

Product and Process Engineering Concepts Brochure "Measures Foam and Entrained Gases Pulse)))) Air", 1998.

PAPEC Brochure "Defoamer Control System D.C.S." (no date available).

(List continued on next page.)

*Primary Examiner*—Steven P. Griffin
*Assistant Examiner*—M. Halpern
(74) *Attorney, Agent, or Firm*—Kilyk & Bowersox, P.L.L.C.

(57) ABSTRACT

A method and an apparatus are provided for measuring the amount of entrained gases in a liquid sample. A conduit defining a volume is provided. The conduit has an inlet at a lower end thereof and an outlet at an upper end thereof. Liquid sample is made to flow into the inlet, through the conduit, and out of the outlet. The weight of the liquid sample in the conduit is determined during a flow of liquid sample through the conduit to obtain a first measurement. Thereafter, a difference between the first measurement and a predetermined weight value representing a weight of the same liquid sample flowing through the conduit but containing no entrained gases is determined to obtain a calculated weight of entrained gases in the liquid sample flowing through the conduit.

27 Claims, 5 Drawing Sheets

OTHER PUBLICATIONS

Pietikäinen, Tapio, "On–line Air Entrainment Tests on Paper Machines", Tappi Journal, Nov. 1992, pp. 185–191.

Woodward, Tom, "Mill closure: The critical issues", PIMA Magazine, Jun. 1996, pp. 44–45.

Gardberg, Lori, "Water–based fixes for foam control", PIMA Magazine, Aug. 1995, pp. 66–67.

Bliss, Terry, "What Is The Effect Of Entrained Air On The Performance Of Hydrocyclones", Recycled Paper Technology, pp. 298–300 (1999).

"Continuous Air Measurement System, KOLB KLG–90, Monitoring Your Paper Production", Michelman (no date available).

* cited by examiner

METHOD AND APPARATUS FOR MEASURING THE AMOUNT OF ENTRAINED GASES IN A LIQUID SAMPLE

BACKGROUND OF THE INVENTION

The present invention relates to a method and apparatus for measuring the amount of entrained gases in a liquid sample.

Entrained gases are usually mentioned in the context of papermaking processes involving a flow of stock, and typically include free air and bound, residual or stabilized air. The stock flow usually includes a slurry of fibers, charged micro-particles such as talc, magnesium carbonate or calcium carbonate, coagulants and/or flocculants such as charged polymers, and starches, all of which are carried in a liquid medium such as water. Turbulent flows in open channels, leaking pumps, and the free-fall of stock or additives into a chest are among the conditions that contribute to the entrainment of air in papermaking stock. Intense agitation of the stock generates shear forces, which can subdivide incoming air bubbles and attach them to components of the stock. The free air portion or unstabilized portion of the entrained gases consists of freely moving air bubbles or free bubbles in the stock, which typically have an individual bubble diameter larger than 70 to 100 $\mu$m. The stabilized air portion of the entrained gases in turn includes air bubbles that are small enough to adhere to fibers, or to be found inside fibers. The average diameter of the bubbles making up the stabilized air portion is typically less than 70 to 100 $\mu$m, with the most common diameter distribution being from about 30 $\mu$m to about 170 $\mu$m. In addition to entrained gases, the stock may also contain dissolved gases. Chemical or biological activity may also produce dissolved gases directly in the stock. Dissolved gases are in the form of molecules in the liquid. The equilibrium between the entrained gases and the dissolved gases depends, among other things, on the prevailing temperature and pressure, and conductivity.

The measurement of entrained gases in liquids is useful in various applications, such as, for example, in the papermaking industry. General experience has shown that the adverse effects of entrained gases on papermaking stock and final sheet production include, among other things, the generation of foam, spots on paper sheets, pin holes, retarded drainage, energy losses in pumps, and sheet breaks. Gas bubbles trapped inside formed paper sheets decrease the number of fiber bonds, decrease the formation of fiber bundles, and decrease the build-up of fiber bundles. Additionally, dissolved gases in paper making stocks tend to maintain aerobic slime and bacteria growth, causing not only quality problems but also more frequent boil-outs and increased consumption of boil-out compounds and cleaning agents. Therefore, an accurate measurement of the actual amount of entrained gases in a papermaking stock is desirable in preventing the above-stated negative effects.

Devices and methods for measuring the amount of entrained gases in a liquid sample are known. According to one method, the Coriolis force necessary to maintain a resonant frequency of a fluid-filled tube is measured and the force or resonant frequency required is used as an indicator of density. This method aims at measuring density to arrive at a determination of the amount of entrained gases in the liquid sample being considered. By way of example, a vibrating U-tube densitometer has recently been proposed for the measurement of entrained gas bubbles. A U-tube is an example of a device that measures resonant frequency to determine density. According to another method called the "Broadway" or "expansion" method, a sample is taken of a liquid and a fixed volume thereof is isolated in a sample chamber under atmospheric pressure. A sudden vacuum is then applied to the sample, which results in an expansion of the entrained gases. The increased volume of the sample is used to measure the amount of entrained gases and dissolved gases in the sample.

According to yet another method, a liquid sample is taken under pressure, such as with a mechanical screw or piston. The decrease in the volume of the sample owing to the pressure increase is measured, and the volume of entrained gases is determined from the measured decrease in volume. The rotation rate of the mixing pump in the papermaking system has also been used to estimate changes in the content of entrained gases, as these parameters correlate relatively well.

A further method involves determining a weight difference of a liquid sample. A liquid sample containing entrained gases is weighed on a scale. The same kind of sample with de-gased liquid is also weighed. The de-gased stock may be obtained by boiling the stock under vacuum to remove any gases therefrom. The gas content is then determined from the weight difference.

Disadvantages of the above existing methods for measuring the amount of entrained gases in a liquid sample include, among other things, an inability to obtain accurate measurements of the actual amount of entrained gases in a liquid sample where the sample is taken from a dynamic liquid system, that is, from a liquid system where the liquid is flowing and where the amount of entrained gases in the liquid may change as a function of time. Typical of a dynamic liquid system would be a paper stock processing system that includes a flow of stock having water as the carrier medium. In such a system, the air content in the flowing liquid is not constant, and varies throughout the process. Random changes in air volume in a paper stock processing system have been measured as being typically between 5 and 20%, but could be as much as 200%, with changes in air volume having the capacity to be either fast or slow. In such a system, existing methods for measuring the amount of entrained gases would be disadvantageous, in part because the method is based on an isolated, stationary stock sample, the quality of the results therefore depending largely on how well the sample represents the average stock at any given time. Additionally, any stationary liquid sample could lead to an escape of entrained gases after even a short period of time, therefore further altering any measurements of entrained gases within that sample.

One method of obtaining measurements of the actual amount of entrained gases in a liquid sample involves the use of on-line sensors. Examples of such sensors include ultrasonic sensors and sensors for sensing sample compressibility.

The principle of operation of ultrasonic sensors is based on the fact that ultrasonic energy will attenuate in a liquid containing entrained gas bubbles, with the attenuation being a function of the amount of gas bubbles. According to this method, a liquid sample is fed from a dynamic liquid system, such as a paper stock processing system, through an ultrasonic sensor for measuring the amount of entrained gas bubbles in the sample. However, although the attenuation of ultrasound is very sensitive to the quantities of stabilized air bubbles present, it is insensitive to free bubbles. In addition, the attenuation efficiency of the air bubble measurement is typically a function of the papermaking system within which the stock flow occurs because the efficiency depends on the distribution of the bubble size and on the mechanism of stabilization of the air bubbles. While the quantity of gaseous air is linearly correlated with the attenuation of ultrasound when the air content is below about 0.9% by volume, if the air content is larger, the number of large, free bubbles increases and the dependence of attenuation on air content is no longer valid.

In addition, on-line sensors are known which make a measurement of entrained gases by compressibility of the process liquid. An example of such a sensor is the PULSE AIR™ sensor, provided by Product and Process Engineering Concepts. The PULSE AIR™ sensor is inserted directly into the process liquid, and determines the amount of entrained gases therein by measuring fluid compressibility. Unfortunately, it is not a continuous measuring system.

SUMMARY OF THE INVENTION

The present invention provides a method for measuring the amount of entrained gases in a liquid sample. The method comprises the steps of providing a conduit defining a volume, the conduit having an inlet at a lower end thereof and an outlet at an upper end thereof; flowing liquid sample into the inlet, through the conduit, and out of the outlet; and determining the weight of liquid sample in the conduit during a flow of liquid sample through the conduit to obtain a first measurement. Thereafter, a difference between the first measurement and a predetermined weight value representing a weight of the same liquid sample flowing through the conduit but containing no entrained gases is determined. The determined difference is then used to obtain a calculated weight or volume of entrained gases in the liquid sample flowing through the conduit.

The present invention further provides an apparatus for measuring the amount of entrained gases in a liquid sample. The apparatus comprises a conduit defining a volume and comprising an inlet at a lower end thereof and an outlet at an upper end thereof; and a weight measuring device coupled to the conduit for measuring a weight of liquid sample flowing through the conduit from the inlet thereof to the outlet thereof to obtain a first measurement. The apparatus further includes a control unit coupled to the weight measuring device. The control unit determines a difference between the first measurement and a predetermined weight value representing a weight of the same liquid sample flowing through the conduit but containing no entrained gases. The difference is used to obtain a calculated weight or volume of entrained gases in the liquid sample flowing through the conduit.

In addition, the present invention provides a system comprising: the apparatus of the present invention as described above; a flow of liquid in a main processing circuit of a processing system; and a diverting device for diverting at least a portion of the flow of liquid in the main processing circuit as a liquid sample through the apparatus.

It is to be understood that both the foregoing general description and the following detailed description are exemplary and explanatory only and are only intended to provide a further explanation of the present invention, as claimed. The accompanying drawings, which are incorporated in and constitute a part of this application, illustrate several exemplary embodiments of the present invention and together with description, serve to explain the principles of the present invention.

BRIEF DESCRIPTION OF THE DRAWINGS

The invention may be more fully understood with reference to the accompanying figures. The figures are intended to illustrate exemplary embodiments of the present invention without limiting the scope of the invention.

DETAILED DESCRIPTION OF THE PRESENT INVENTION

Entrained gases volumetrically displace a liquid sample in a measuring conduit, thereby reducing the weight of the liquid sample relative to when it contains no entrained gases. According to the present invention, a reduction in the overall measured weight of a liquid sample flowing in a conduit is calculated as an indication of the amount of entrained gases within the liquid sample.

The present invention provides a method for measuring the amount of entrained gases in a liquid sample. A conduit defining a volume is provided. The conduit has an inlet at a lower end thereof and an outlet at an upper end thereof. Liquid sample is made to flow into the inlet, through the conduit, and out of the outlet. The weight of the liquid sample in the conduit is determined during a flow of liquid sample through the conduit, to obtain a first measurement. Thereafter, a difference between the first measurement and a predetermined weight value representing a weight of the same liquid sample flowing through the conduit but containing no entrained gases is determined. The difference is then used to obtain a calculated weight or volume of entrained gases in the liquid sample flowing through the conduit.

The present invention further provides an apparatus for measuring the amount of entrained gases in a liquid sample. The apparatus comprises a conduit defining a volume and comprising an inlet at a lower end thereof and an outlet at an upper end thereof. A weight measuring device is coupled to the conduit for measuring a weight of liquid sample flowing through the conduit from the inlet thereof to the outlet thereof to obtain a first measurement. The apparatus further includes a control unit coupled to the weight measuring device for determining a difference between the first measurement and a predetermined weight value. The predetermined weight value represents a weight of the same liquid sample flowing through the conduit but containing no entrained gases to obtain a calculated weight of entrained gases in the liquid sample flowing through the conduit.

In addition, the present invention provides a system comprising an apparatus of the present invention as described above, a flow of liquid through a main processing circuit or flow line of a processing system, and a diverting device for diverting at least a portion of the flow of liquid in the main processing circuit or flow line through the apparatus as a liquid sample.

Figure 1:
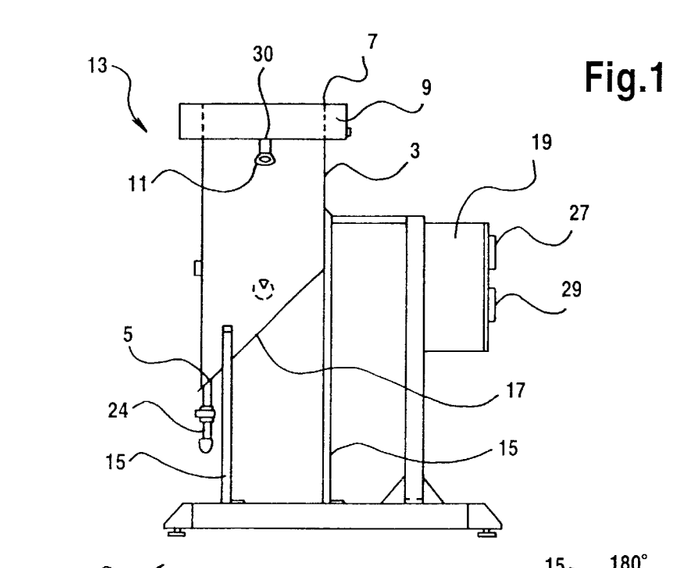
FIG. 1 is a side elevational view of a preferred embodiment of an apparatus according to the present invention.
Figures 2, 3A:
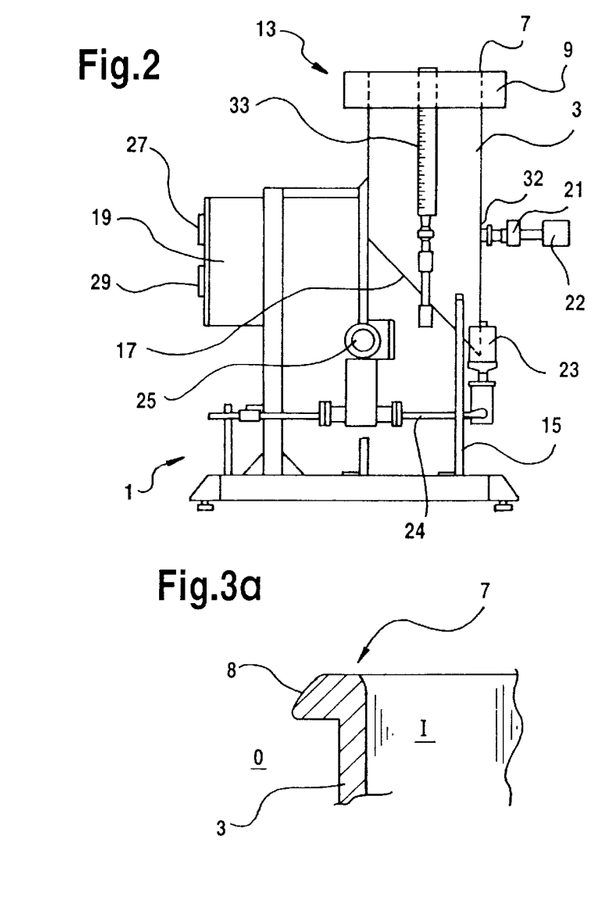
FIG. 2 is a view similar to FIG. 1, showing the apparatus from a side opposite to the side shown in FIG. 1.
FIG. 3a is a partially cut-away longitudinal cross section of a preferred embodiment of the lip portion for the weir shown in FIG. 3.

Referring now to FIGS. 1–5, a preferred embodiment of an apparatus for measuring the amount of entrained gases in a liquid sample according to the present invention is exemplified. As depicted in FIG. 1, the apparatus 1 comprises a cylindrical conduit 3 in the form of a vertical column having an inlet 5 at a lower end thereof and an outlet 7 at an upper end thereof. In the shown, preferred embodiment, conduit 3 is in the shape of a vertical column. Outlet 7 preferably includes a weir over an upper lip portion 8 of which the liquid sample flows out into a catch basin 9 before exiting the catch basin 9 through nipple 30 and outlet pipe 11. The conduit and catch basin assembly 13 is preferably made of stainless steel or aluminum, and mounted on a support base by way of support legs 15. As best seen in FIGS. 1 and 2, conduit 3 has a bottom portion 17 that is a planar surface slanted with respect to a horizontal plane. The bottom surface of conduit 3 is preferably slanted to prevent settling of particulate matter. The pressure transducer 21 is preferably placed, as shown, in an area of reduced turbulence to preferably reduce effects of turbulence on pressure transducer performance.

Conduit 3 represents a sample chamber or volume through which the sample liquid to be measured flows. What is meant by "liquid" in the context of the present invention encompasses any readily flowing substance, including but not limited to paper stock slurry, supply water, effluent flow, emulsions, resins, liquid coating compositions, black liquor, including spent cooking medium from a Kraft process, and red liquor. Conduit 3 displays structural features designed to limit any settling of matter carried as part of the sample liquid should the sample liquid be prone to separation. By way of example, as noted above, paper stock typically includes a slurry of fibers, charged micro-particles such as talc, magnesium carbonate or calcium carbonate, coagulants and/or flocculants such as charged polymers, and starch all carried in a liquid medium such as water. One or more of these components could potentially settle at the bottom of conduit 3 if the above-mentioned features according to the present invention are not included.

In addition, apparatus 1 has been provided with other advantageous features that allow it to dampen the effects of small variations in liquid sample flow through the conduit. These features include, but are not limited to, lip design and angle at outlet 7 of conduit 3, as suggested by referring to FIGS. 3 and 3a. Lip designs as shown preferably provide a horizontal flow of liquid sample, thereby dampening vertical pulsation that would be read by the pressure sensor. These features advantageously allow a more accurate measurement of weight with respect to the liquid sample flowing through the conduit.

Figure 3:
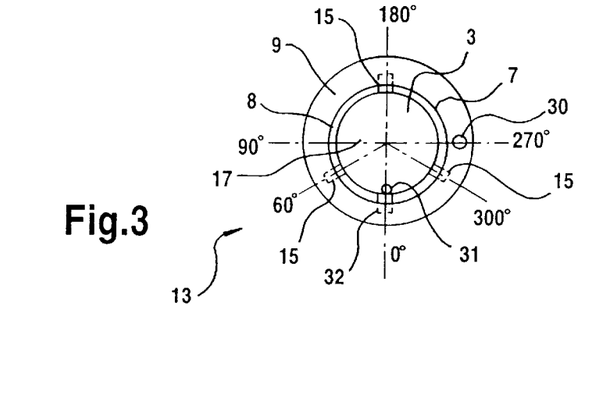
FIG. 3 is a top plan view of the apparatus of FIG. 1.

Referring now to FIG. 3, a top view of the conduit and catch basin assembly 13 is shown. As seen in FIG. 3, outlet 7 shaped in the form of a weir defines a lip portion 8 that presents a smooth surface for the outflow of the liquid sample from the conduit 3 onto the catch basin. Nipple 30 is welded onto a pan ring portion of catch basin 9, and a nipple 31 is welded at the lowest point of the bottom portion 17 of conduit 3 as shown. Nipple 31 is in communication with piping 24 connected to a control valve 23 and flow-meter 25, as will be described in further detail below. The support legs 15 are further shown in FIG. 3 as is a welded bung 32 for a pressure transducer 21, as will be further described in detail below.

As seen in FIG. 3a, a cross-section of a portion of lip 8 is shown. Liquid sample flows from the inner region I of the conduit 3 over lip 8 onto the outer region O of conduit 3. FIG. 3a shows a preferred, but not a limiting, angling and design of the lip portion to allow a dampening of small variations in the flow of liquid sample. The lip 8, and/or the interior of conduit 3, may be formed of, or coated with, a hydrophobic material such as Teflon®, Kynarg®, a hydrophobic ceramic material, a hydrophobic plastic material, and the like.

Figure 4:
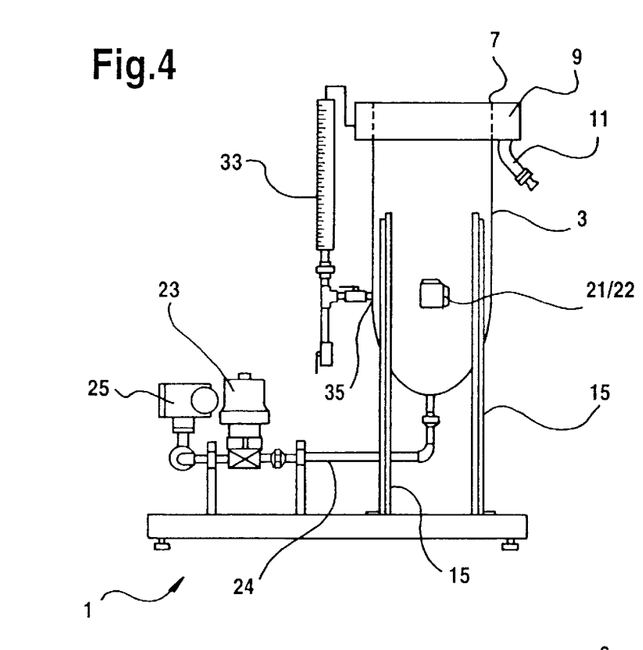
FIG. 4 is back elevational view of the apparatus of FIG. 1.
Figure 5:
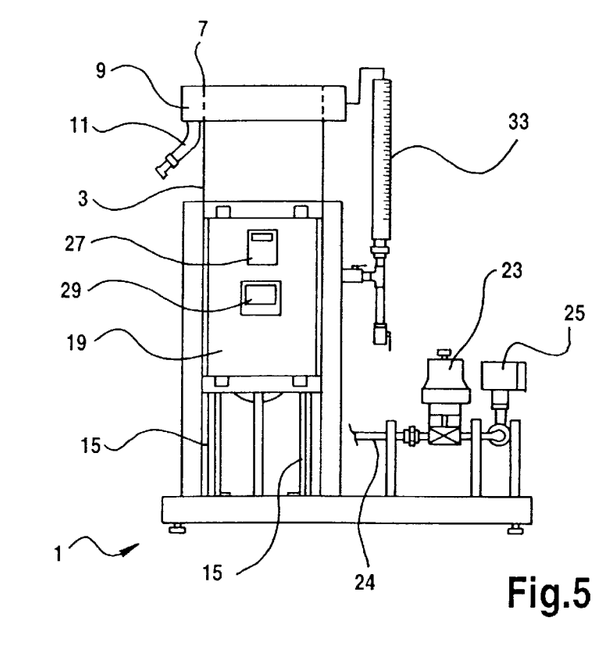
FIG. 5 is a front elevational view of the apparatus of FIG. 1.

As further seen in FIGS. 2, 4 and 5, the preferred embodiment of the apparatus according to the present invention further comprises a weight measuring device in the form of pressure transducer 21 coupled to the conduit 3 for measuring a pressure of liquid sample therein. Preferably, as seen in FIG. 2, the level at which the pressure of the liquid sample within the conduit is determined by the pressure transducer corresponds to the highest point of slanted bottom portion 17 of the conduit 3 and/or a location of reduced or minimal turbulence. A control valve 23 controls the amount of flow through the inlet 5 of the conduit. Control valve 23 is preferably a ball valve, but may in the alternative include a diaphragm, butterfly, pinch, needle, gate, V-ball or iris control, or other suitable valve depending on application needs. A flow-meter 25 is further coupled to the conduit 3 for measuring, indicating and/or transmitting signals to control unit 19 regarding the actual flow rate of liquid sample through the conduit at any given point in time, on a continuous basis. Flow-meter 25 is preferably a magnetic flow-meter, but may, in the alternative, include a Coriolis mass flow-meter, a vortex meter, gear meter or Doppler radar meter depending on application needs. The control valve 23 and flow-meter 25 are coupled to the conduit 3 through piping 24 which leads to inlet 5 and which, in the shown preferred embodiment, is in communication with the liquid sample inside the conduit at a lowest point of the conduit corresponding to a lowest point of the bottom surface 17 thereof. Preferably, the piping 24 is in a location that has a relatively reduced amount of turbulence.

As best seen in FIGS. 2 and 4, the preferred embodiment of the apparatus according to the present invention further includes a graduated cylinder that is in communication with the flow of liquid sample in conduit 3 through a bung 35 (FIG. 4). The function of the graduated cylinder is to remove a measured amount of fluid to simulate the displacement of that fluid corresponding to a change in entrained air found in calibrating the unit.

Control unit 19 is in signal communication with the weight measuring device 21, and contains the necessary control logic, as would be recognized by one skilled in the art, to measure the weight of the liquid sample in the conduit to arrive at a first measurement, and to determine a difference between the first measurement and a predetermined weight value representing a weight of the same liquid sample flowing through the conduit but containing no entrained gases. The control unit is therefore adapted to obtain a calculated weight of entrained gases in the liquid sample flowing through the conduit, preferably as a percent by weight value. The control unit may be programmed to obtain the calculated weight of entrained gases either on a continuous basis, or on an intermittent basis, depending on application needs. The control logic of the control unit 19 may be further adapted to evaluate the signal corresponding to the calculated weight of entrained gases. Such evaluation preferably encompasses comparing the calculated weight of entrained gases with a predetermined maximum threshold weight, as will be explained in further detail below. Control unit 19 may then send a signal to another control device, such as, for instance, a control device in a processing system from which the liquid sample is taken. An example of such a control device would be an defoamer dispensing device for dispensing defoamer into the flow of liquid in a papermaking system, or a control device that otherwise chemically and/or mechanically alters the process of the papermaking system as a function of whether the calculated percent by weight entrained gases has reached and/or surpassed a given threshold. An example of a threshold or maximum percent by weight of entrained gases in a papermaking stock above which defoamer should preferably be discharged into the stock would preferably be from about 0% to about 15%.

Control unit 19 is preferably further operatively coupled to the control valve 23 so that it can control the flow of the liquid sample through conduit 3. The flow is preferably controlled to maintain a constant weir height and to minimize variations in pressure read by the transducer. The control unit may be equipped with one or more proportional integral derivative (PID) process control algorithm controllers, programmable logic software relay logic process controllers, or other process controllers depending on application needs, including real-time error correction controllers.

As seen in FIG. 5, a preferred embodiment of the control unit 19 according to the present invention includes a display unit 27 disposed or mounted on a side of control unit 19 for allowing a display of the calculated weight of the entrained gases either on a continuous basis, or on an intermittent basis, depending upon factors sensed by the programming of the control unit 19. Additionally, the controls may be replaced or modified to accommodate characteristics of a given process for which apparatus 1 may be used depending on application needs. Apparatus 1 can control pH, temperature, conductivity, consistency, and other properties. Moreover, control unit 19 is preferably provided with a chart recorder 29. The function of the chart recorder 29 is to document the history of the data manipulated by control unit 19, such as, for example, the data stream of measured percent by weight entrained gases and of the points in time during which a control device such as an additive dispensing device was activated by the control unit. Chart recorder 29 is part of a data acquisition feature of the control unit, which would allow it to archive the history of its performance as noted above.

A pressure transducer in the form of, for example, a differential pressure (DP) cell, can be used to measure the weight of a column of liquid in the conduit.

Signal regeneration means may be provided so a signal, such as indicative of the weight of liquid in the conduit, sensed by a control unit, can be shared with another device, such as an adjusting unit.

According to a preferred embodiment of the invention, as shown in the FIGS., additional sensor elements 22 may be coupled to the conduit to allow the measurement of pH, conductivity, density and/or temperature relating to the liquid sample. Any suitable location for mounting the sensors can be chosen, for example, as shown in the Figures. Sensor elements 22 may further be in signal communication with control unit 19 in order to transmit thereto signals corresponding to the sensed parameters. The control logic in control unit 19 may then utilize the sensed values in order to arrive at a measurement of the weight of entrained gases based on those values. The pH, conductivity, density, and temperature can affect the physical properties of a liquid and entrained air formation in that liquid. In the alternative, the thus sensed values may be used for monitoring purposes only.

Figure 6A:
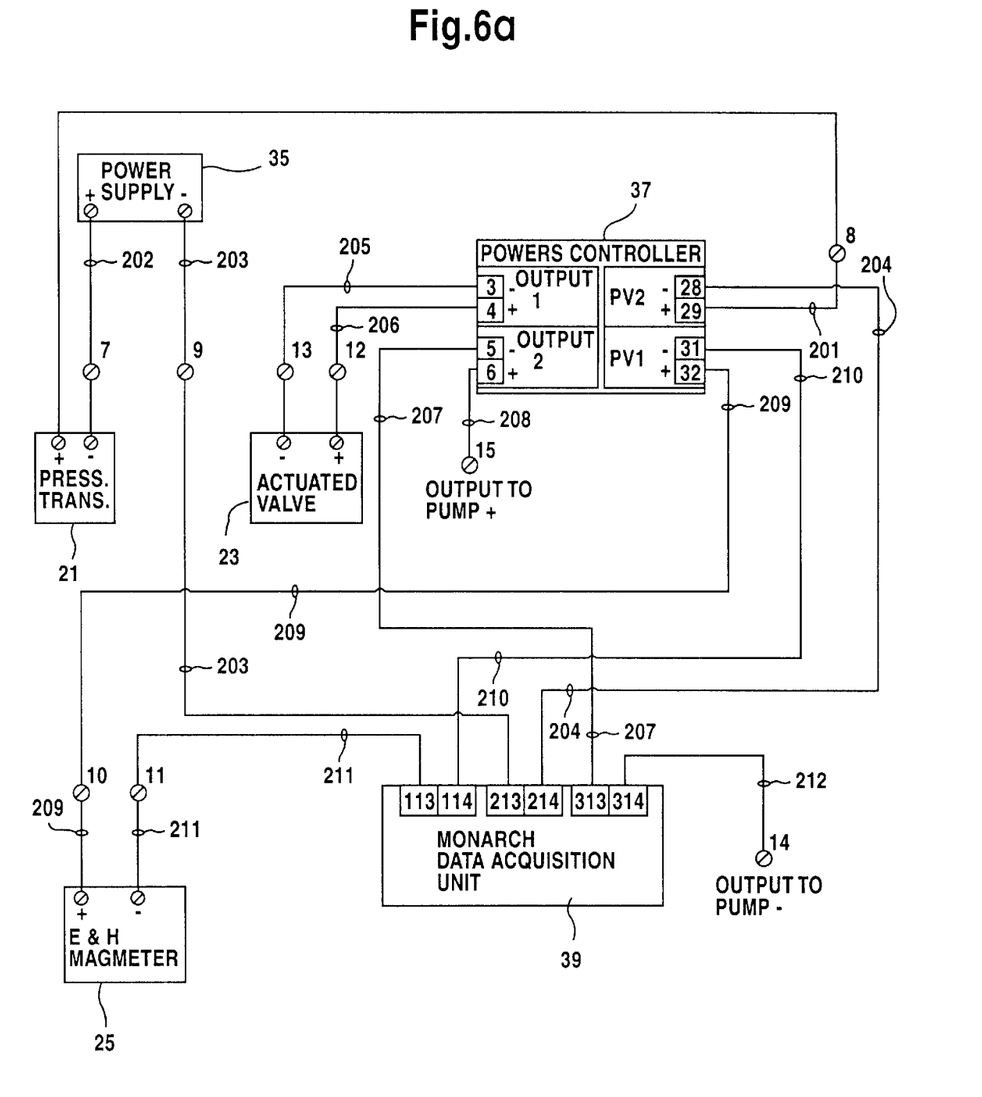
FIG. 6a is a schematic representation of a preferred embodiment of an electrical circuit incorporating the power supply, sensors and controls in the apparatus of FIG. 1.
Figure 6B:
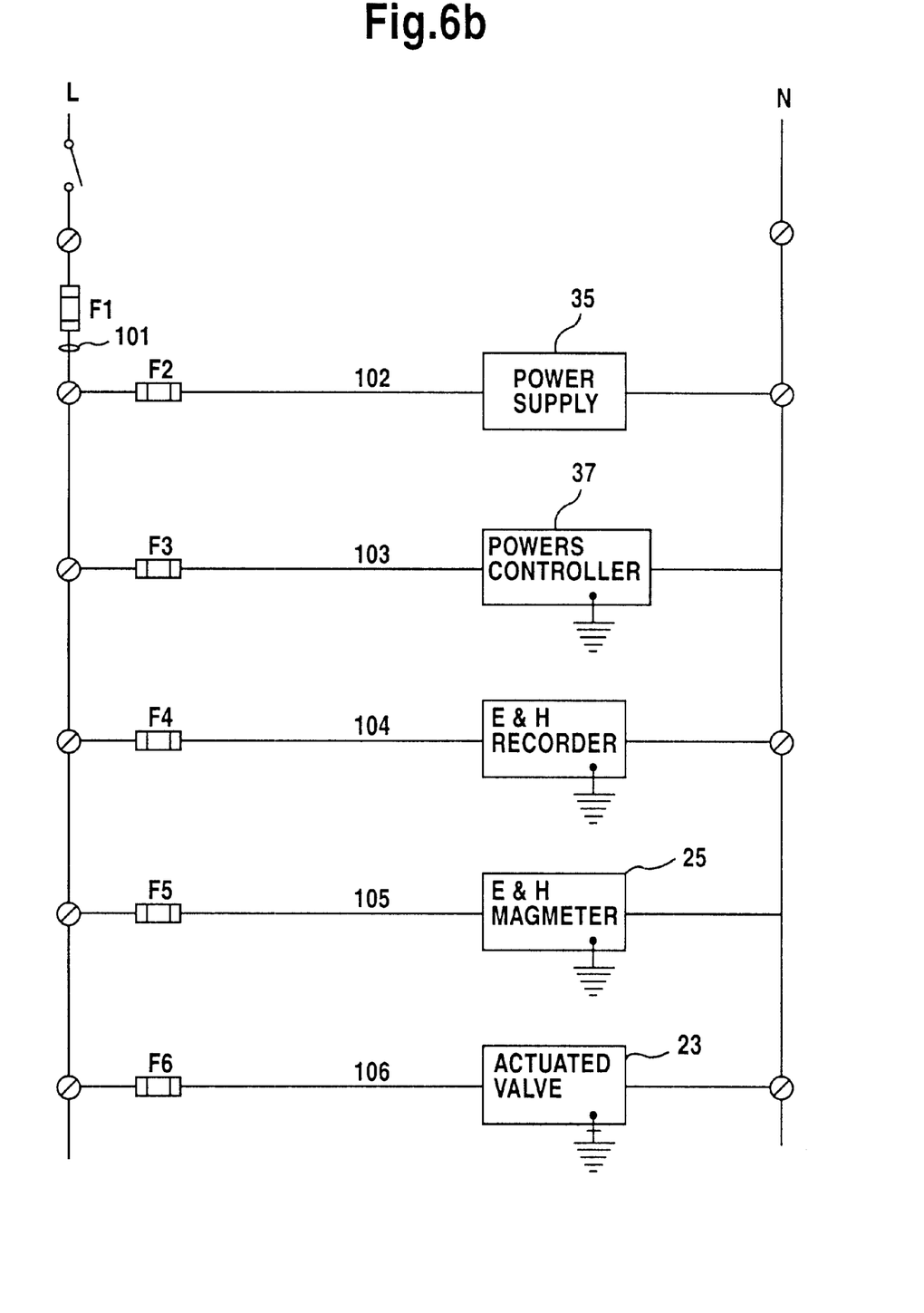
FIG. 6b is a representation of a preferred embodiment of an electrical circuit showing the power supply, sensors and controls disposed in parallel.

In the embodiment illustrated, FIGS. 6a and 6b are each a part of control unit 19. FIGS. 6a and 6b show the electrical circuit linking pressure transducer 21, control valve 23, flow-meter 25 with power supply 35, powers controller 37, and data acquisition unit 39 in a manner readily recognizable by one skilled in the art. FIG. 6a shows power circuitry and FIG. 6b shows communications circuitry, with both sets of circuitry preferably being housed in the same housing or box. Preferably, the powers controller and data acquisition unit are part of control unit 19. In FIGS. 6a and 6b, reference numerals 202, 203, and 205 represent wire numbers and reference numerals 7, 9, 12, and 13 represent terminals. F1, F2, and F3 represent fused terminal numbers. As seen in particular in FIG. 6b, the components of the circuit are preferably to be connected in parallel according to the present invention, for example, wherein the left-side of a circuit such as shown in 6b includes a 4–20 mA loop and the right-side shows a ladder logic circuit.

Figure 7:
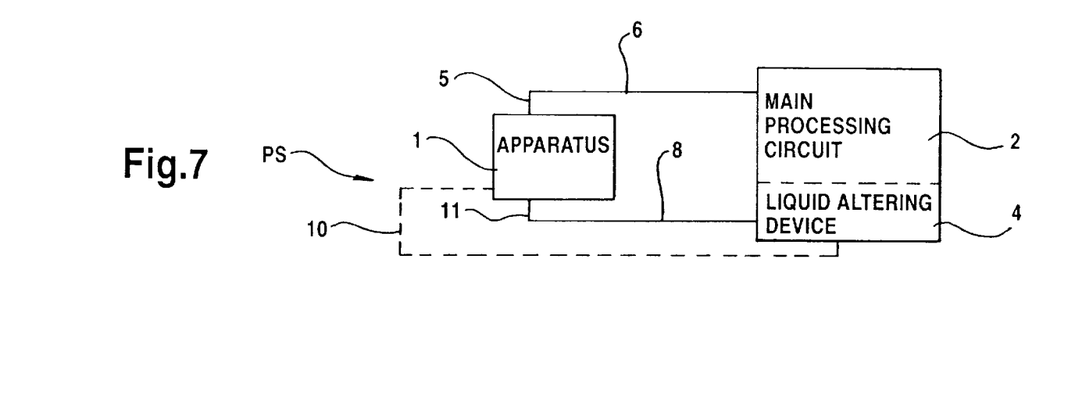
FIG. 7 is a schematic representation of a processing system incorporating a main processing circuit and the apparatus according to the present invention.

FIG. 7 shows a schematic representation of an operative environment within which the apparatus of the present invention may be used. As seen in FIG. 7, apparatus 1, the preferred embodiment of which is shown in FIGS. 1–6b, is disposed in parallel with respect to a main processing circuit or processing system, such as a processing circuit for papermaking stock. Thus, according to a preferred embodiment of the present invention, the liquid sample in apparatus 1 represents a portion of the liquid flowing in the main processing circuit 2, which is diverted through extracting line 6 for delivery to conduit 3 of apparatus 1 through inlet 5 of the conduit. The liquid sample then flows through apparatus 1, and exits through outlet pipe 11 to a return line 8, which returns the measured liquid sample to merge with the liquid in the main processing circuit 2 as shown. The processing system in the embodiment shown includes the main processing circuit 2, the apparatus 1, and lines 6 and 8. Preferably, the main processing circuit further includes a liquid altering device 4, which may comprise, by way of example, an additive dispensing device such as a pump and a defoaming agent. The liquid altering device is preferably in signal communication via conventional means, such as lines 10 shown as broken lines, with control unit 19, which controls the liquid altering device to alter the liquid in the liquid processing system as a function of the weight of entrained gases measured by apparatus 1.

In an embodiment of the present invention, a magnetic flowmeter is used to measure flow to the conduit. The meter sends a 4–20 mA signal to the PID controller. The PID controller can compare that signal to a user-defined setpoint.

The operation of apparatus 1 will now be described in connection with its use in the liquid processing system of FIG. 7. A liquid sample is initially extracted via line 6 from liquid flowing in a main processing circuit 2, and directed to apparatus 1. The liquid sample then flows into conduit 3 via inlet 5, and, by virtue of the shape of conduit 3, is directed upward toward outlet 7. The slanted bottom portion 17 of conduit 3 in turn ensures that nothing settles in the bottom of the conduit. The slanted bottom reduces possible particulate settling and allows liquid to enter the conduit in a less turbulent manner. As the liquid sample flows upwardly, it exits the conduit from outlet 7 and over lip 8 of the weir of outlet 7, whereupon it flows into catch basin 9. Here, the liquid sample reaches nipple 30, and is directed out of apparatus 1 through outlet pipe 11, and into return line 8 to be converged with the main processing circuit of the liquid processing system. The liquid flowing in the main processing circuit may acquire entrained gases therein as it is being processed in circuit 2. For example, if circuit 2 is a papermaking circuit, the liquid flowing therein may acquire entrained gases therein at various stages in the process. Some air and gases may get mixed into the stock in the stock preparation process prior to the silo. A typical mixer of air, such as a chest agitator may run blades close to or partly above the surface in the chest, entraining air into the liquid. In addition, other sources of entrained air may include pipes discharging water or stock above the surface of the stock, some overflow arrangements, leaking seals operating under vacuum, white water circulation, and centrifugal cleaners.

As the liquid sample flows through conduit 3, pressure transducer 21 measures the pressure of the liquid sample within the conduit at the level of bung 32. The measured pressure is multiplied by the horizontal surface area of the conduit at the level of bung 32 to obtain the weight of the liquid sample flowing through the conduit. For example, if the column is of vertical, cylindrical shape, then the higher the column, the more weight that is read by the transducer. This weight represents a first measurement. A signal corresponding to a value representing the first measurement is then transmitted to control unit 19 and control unit 19 uses this signal to evaluate the first measurement in comparison with a predetermined weight value of the same liquid sample flowing through the conduit but containing no entrained gases. The difference is used to obtain a calculated weight of entrained gases in the liquid sample. The determination of the weight of the same liquid sample but containing no entrained gas can be calculated and programmed into the control logic of control unit 19.

A method of determining the weight of the same sample liquid but containing no entrained gas is to simply calculate the weight based on a theoretical measurement of the volume of the components comprising the sample and their respective weights. In another calculation method, a sample of the stock is heated under vacuum to remove entrained gases and form a treated sample, a specified volume of which can then be weighed to determine a density. The density measurement can then be used to determine the weight of the same liquid sample but containing no entrained gases by multiplying the measured density of the treated sample by the volume of the conduit 3 or effective volume of conduit 3. Instead, a sample of known volume could be taken and weighed to determine the weight of a sample containing no entrained gases.

The predetermined weight value may be determined in one of a number of ways. Preferably, the predetermined weight value is determined by volume, displacement, or weight.

According to a preferred embodiment, a determination of the calculated weight encompasses a determination of the percent by weight of entrained gases in the liquid sample. Depending on the calculated weight of entrained gases in the liquid sample, the control logic in the control unit 19 may direct the control unit to send an activation signal to liquid altering device 4 to alter the liquid in the liquid processing system. For example, where a pump and source of additive such as a defoaming agent are used as the liquid altering device, the control unit may activate the pump to dispense additive into the liquid of the liquid processing system. In addition, or in the alternative, the liquid altering device may mechanically alter the amount of entrained gases in the liquid flowing in the liquid processing system. Preferably, the activation signal from control unit 19 is generated as a result of a comparison within the control logic of control unit 19 of the calculated weight of entrained gases with a predetermined maximum threshold weight, keeping in mind that "weight" in this context encompasses percent by weight air in the liquid sample. Any suitable algorithm known to those skilled in the art can be used by the control unit, for example, algorithms of simple mathematic function. The predetermined maximum threshold weight is a function of the characteristics of the main processing circuit. The predetermined maximum threshold weight will vary from unit to unit, depending on the physical size of the unit and the physical properties of the liquid. The maximum weight that the unit can handle can be used as a base line for determining a suitable predetermined maximum threshold weight. For example, where the main processing circuit is a papermaking processing circuit, a preferred range for the predetermined maximum threshold weight would be from about 0.1 weight percent to about 15 weight percent. If the amount of entrained air exceeds the PMTW, it would be desirable to activate defoaming devices or other entrained air reduction mechanisms within the system, or to activate a signal indicative of an undesirable amount of entrained air. In a papermaking system, therefore, the predetermined maximum threshold weight represents the weight or percent by weight of entrained gases, which reduce the weight of the liquid, and above which the associated adverse effects to the papermaking process would be a problem.

The liquid altering device, according to a preferred embodiment of the present invention, may include a device for achieving de-aeration of the liquid flowing in the liquid processing system, such as a defoamer, as previously stated. De-aeration may be achieved using either de-aeration chemicals such as finely dispersed emulsions, as described, for example, in the article entitled *Deaeration in High Temperature Systems*, Lorenčak et al., Paper Technology, November 1997, or through physico-mechanical de-aeration, for example as described with respect to the DECULATOR® de-aeration device described in the articles of Matula entitled *Presence of Entrained Air and Dissolved Gases in Paper Making Stock*", *Paper Southern Africa*, Vol. 18, No. 3, June 1998, pp 14–19, and Vol. 18, No. 4, August 1998, pp 9–14, the teachings of which are hereby incorporated in their entireties by reference. The de-aeration process is designed to substantially remove entrained gases and dissolved gases, preferably completely.

Figure 8:
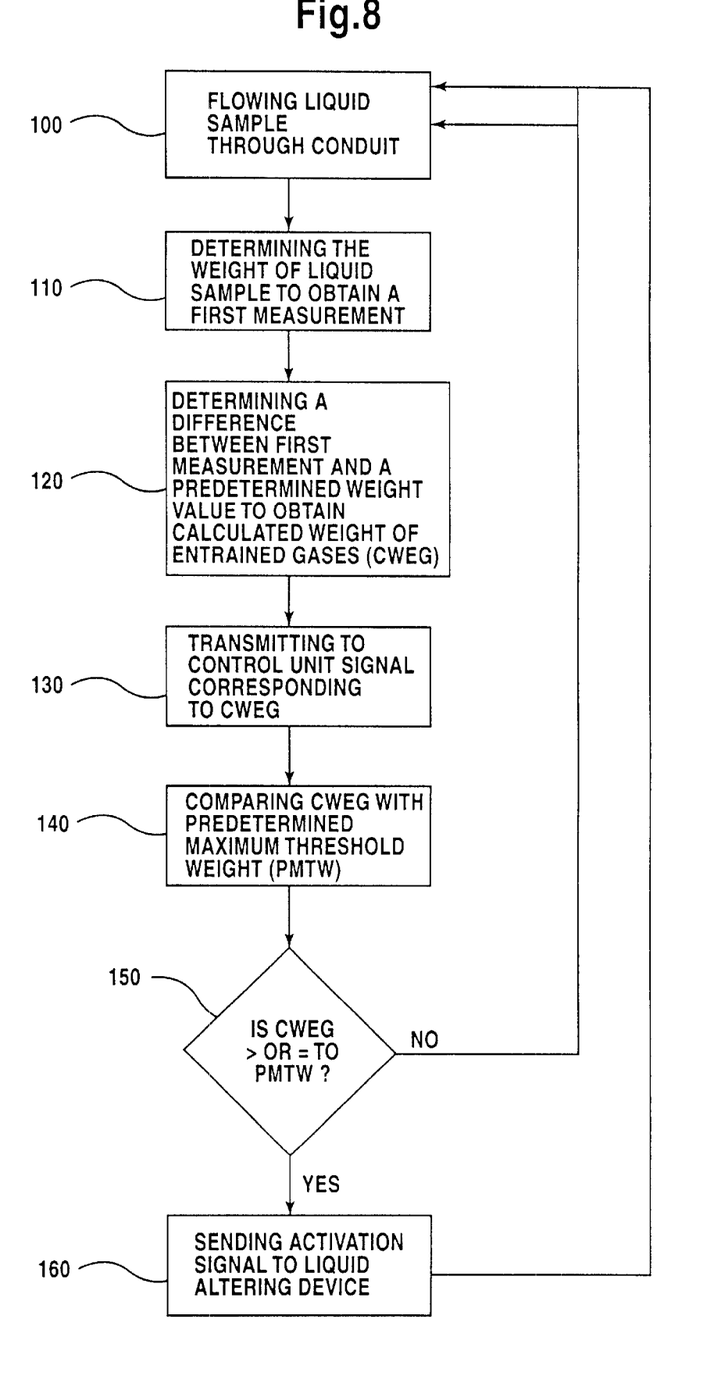
FIG. 8 is a flowchart showing the steps of a preferred embodiment of a method according to the present invention.

A flow chart showing the method steps carried out according to a preferred embodiment of the present invention is provided in FIG. 8. At step 100, liquid sample flows through the conduit of an apparatus according to the present invention. This step may be a continuous step or an intermittent step, depending on the needs of the application. Thereafter, at step 110, a first measurement is obtained from a determination of the weight of the liquid sample flowing through conduit 3. At step 120, a difference between this first measurement and a predetermined weight value is determined to obtain a calculated weight of entrained gases (CWEG). At step 130, a signal corresponding to the CWEG is transmitted to control unit 19, which then performs steps 140 to 160. Steps 140 and 150 correspond to one alternative for an evaluation of the CWEG by the control unit. At step 140, the CWEG is compared with a predetermined maximum threshold weight (PMTW) for the liquid sample, which represents the maximum weight of entrained gases in the liquid sample, preferably corresponding to a minimum weight of the liquid sample, that the control unit will allow before an activation signal is sent. At step 150, a query is made as to whether CWEG is greater than or equal to PMTW. If so, then, the control unit sends an activation signal at step 160 to a liquid altering device, such as a defoaming dispenser, in order to reduce the amount of entrained gases in the liquid. If CWEG is below PMTW, or after an activation signal has been sent to a liquid altering device, measurements continue to be made by the measuring apparatus.

A shroud may be included to cover and protect component parts of the apparatus or the entire apparatus.

The present invention further includes an apparatus for measuring the amount of entrained gases in a liquid sample comprising means for flowing the liquid sample in a conduit; means for determining the weight of liquid sample in the conduit during a flow of liquid sample through the conduit to obtain a first measurement; and means for determining the difference between the first measurement and a predetermined weight value representing a weight of the same liquid sample flowing through the conduit but containing no entrained gases. The difference is then used to obtain a calculated weight of entrained gases in the liquid sample flowing through the conduit. An example of the means is shown in FIGS. 1–7.

Advantageously, the method and apparatus of the present invention, although based on obtaining a liquid sample, allow an accurate measurement of the actual amount of entrained air within the sample by virtue of the fact that the sample flows through the measuring apparatus. Therefore, the quality of the results obtained using the apparatus of the present invention is more desirable when compared to prior apparatuses that use an isolated, stationary sample for measurements. This is in part due to the fact that a flowing liquid sample is a better representation of the average stock at any given time. Additionally, any stationary liquid sample can have an escape of entrained gases, that is, of gas bubbles therefrom, after only a short period of time, therefore further altering any measurements of entrained gases within that sample. The method and apparatus according to the present invention avoid such a drawback.

In addition, the apparatus of the present invention advantageously allows an accurate measurement of both stabilized and free air bubbles regardless of the bubble size distribution of the entrained air in the sample, and is thus superior to on-line measuring devices such as ultrasound sensors. As noted above, disadvantageously, although the attenuation of ultrasound is very sensitive to the quantities of stabilized air bubbles present, it is insensitive to free bubbles. In addition, the attenuation efficiency of the air bubbles is typically a function of the papermaking system within which the stock flow occurs because this efficiency depends on the distribution of the bubble size and on the mechanism of stabilization of the air bubbles being used. While the quantity of gaseous air is linearly correlated with the attenuation of ultrasound when the air content is below about 0.9% by volume, if the air content is larger, the number of large, free bubbles increases and the dependence of attenuation on air content will no longer be valid. The method and apparatus of the present invention advantageously overcome these drawbacks. The present invention provides a real-time measurement system.

An accurate measurement of the actual amount of entrained air in a processing system such as a papermaking system is desirable for avoiding the adverse effects associated with an unwanted level of entrained air in the paper stock mentioned above. In addition, knowing the actual amount of entrained air advantageously allows an effective regulation of the amount of defoamer to be added to the paper stock. A minimal use of defoamers is beneficial for cost saving reasons, and also because defoamers may interfere with retention and drainage chemicals, and may contribute to additional dirt build-up and accidental pitch problems. The present invention substantially obviates the above issues by providing a reliable way of accurately measuring the actual amount of entrained gases within a liquid sample so that any amount of defoamer introduced in a connected processing system can be effectively regulated as a function of the measured amount of entrained air.

It will be apparent to those skilled in the art that various modifications and variations can be made to the embodiments of the present invention without departing from the spirit or scope of the present invention. Thus, it is intended that the present invention covers other modifications and variations of the invention within the scope of the appended claims and their equivalents.

What is claimed is:

1. An apparatus for measuring the amount of entrained gases in a liquid sample, the apparatus comprising:
   a conduit defining a volume and comprising an inlet at a lower end thereof and an outlet at an upper end thereof;
   a weight measuring device coupled to the conduit for measuring a weight of liquid sample flowing through the conduit from the inlet thereof to the outlet thereof to obtain a first measurement; and
   a control unit coupled to the weight measuring device for determining a difference between the first measurement and a predetermined weight value representing a weight of the same liquid sample flowing through the conduit but containing no entrained gases to obtain a calculated weight of entrained gases in the liquid sample flowing through the conduit;
   and further comprising a liquid altering device for altering the liquid in the processing system as a function of the calculated weight of entrained gases in the liquid sample.

2. The apparatus of claim 1, wherein the liquid sample flowing through the conduit is a portion diverted from a flow of liquid in a main processing circuit of a processing system.

3. The apparatus of claim 1, wherein the liquid altering device is located upstream of the test conduit.

4. The apparatus of claim 1, wherein the liquid altering device is an additive dispensing device for dispensing an additive into the flow of liquid in the processing system as a function of the calculated weight of entrained gases in the liquid sample.

5. The apparatus of claim 4, wherein the additive dispensing device comprises a pump and a supply of additive, wherein the pump is adapted to pump an additive into the flow of liquid in the processing system in response to a signal received from the control unit.

6. The apparatus of claim 5, wherein the additive is a defoaming agent.

7. The apparatus of claim 5, wherein the control unit is adapted to send a signal for activating the pump when the calculated weight of entrained gases exceeds a predetermined maximum threshold weight.

8. The apparatus of claim 7, wherein the predetermined maximum threshold weight corresponds to 0.1 weight percent entrained gases.

9. The apparatus of claim 4, wherein the pressure transducer is a diaphragm pressure transducer.

10. The apparatus of claim 4, wherein the liquid altering device is adapted to mechanically decrease entrained gases in the liquid sample.

11. The apparatus of claim 1, wherein the liquid altering device is located downstream of the test conduit.

12. The apparatus of claim 1, wherein the weight measuring device comprises a pressure transducer.

13. The apparatus of claim 1, wherein the outlet comprises a weir, the apparatus further comprising a catch basin disposed adjacent the weir such that liquid sample flowing out of the outlet flows into the catch basin.

14. The apparatus of claim 1, wherein the conduit contains a liquid sample and the liquid sample is a papermaking stock.

15. The apparatus of claim 1, wherein the upper end of the conduit comprises a hydrophobic material.

16. The apparatus of claim 1, wherein the upper end of the conduit comprises a lip and the lip comprises a hydrophobic material.

17. The apparatus of claim 1, further comprising at least one of a flow-meter coupled to the conduit for measuring an actual flow of the liquid sample through the conduit and a control valve coupled to the conduit for controlling a flow of the liquid sample through the conduit.

18. The apparatus of claim 17, wherein the at least one of the flow-meter and the control valve are in signal communication with the control unit.

19. The apparatus of claim 1, further comprising a sensor coupled to the conduit for measuring at least one of a pH, a temperature, a conductivity, and a density of the liquid sample flowing through the conduit.

20. The apparatus of claim 19, wherein the sensor is in signal communication with the control unit for transmitting a signal thereto corresponding to the at least one of a pH, a temperature, a conductivity and a density of the liquid sample flowing through the conduit.

21. The apparatus of claim 1, wherein the control unit comprises a chart recorder for recording a data stream of a history the calculated weight of the entrained gases in the liquid sample.

22. An apparatus for measuring the amount of entrained gases in a liquid sample, the apparatus comprising:
    a conduit defining a volume and comprising an inlet at a lower end thereof and an outlet at an upper end thereof;
    a weight measuring device coupled to the conduit for measuring a weight of liquid sample flowing through the conduit from the inlet thereof to the outlet thereof to obtain a first measurement; and
    a control unit coupled to the weight measuring device for determining a difference between the first measurement and a predetermined weight value representing a weight of the same liquid sample flowing through the conduit but containing no entrained gases to obtain a calculated weight of entrained gases in the liquid sample flowing through the conduit, wherein the conduit has a slanted bottom portion.

23. The apparatus of claim 22, wherein the weight measuring device is coupled to the conduit at a point corresponding to a highest level of the slanted bottom portion thereof.

24. The apparatus of claim 22, further comprising at least one of a flow-meter for measuring an actual flow of the liquid sample through the conduit and a control valve for controlling a flow of the liquid sample through the conduit, the at least one of the flow-meter and the control valve being coupled to the conduit at a point corresponding to a lowest level of the slanted bottom portion thereof.

25. A system comprising:
    an apparatus;
    a flow of liquid in a main processing circuit of a processing system; and
    a diverting device for diverting at least a portion of the flow of liquid in the main processing circuit as a liquid sample through the apparatus, the apparatus comprising:
        a conduit defining a volume and comprising an inlet at a lower end thereof and an outlet at an upper end thereof;
        a weight measuring device coupled to the conduit for measuring a weight of liquid sample flowing through the conduit from the inlet thereof to the outlet thereof to obtain a first measurement; and
        a control unit coupled to the weight measuring device for determining a difference between the first measurement and a predetermined weight value representing a weight of the same liquid sample flowing through the conduit but containing no entrained gases to obtain a calculated weight of entrained gases in the liquid sample flowing through the conduit;
        and further comprising a merging device for merging liquid sample from the apparatus with the liquid in the main processing circuit downstream of the apparatus.

26. The system of claim 25, wherein the liquid sample is a papermaking stock.

27. An apparatus for measuring the amount of entrained gases in a liquid sample comprising:
    means for flowing the liquid sample in a conduit;
    means for determining the weight of liquid sample in the conduit during a flow of the liquid sample through the conduit to obtain a first measurement; and
    means for determining the difference between the first measurement and a predetermined weight value representing a weight of the same liquid sample flowing through the conduit but containing no entrained gases to obtain a calculated weight of entrained gases in the liquid sample flowing through the conduit;
    and further comprising means for altering the liquid as a function of the calculated weight of entrained gases in the liquid sample.

* * * * *